US00PP19796P2

(12) United States Plant Patent
Bradford

(10) Patent No.: US PP19,796 P2
(45) Date of Patent: Mar. 3, 2009

(54) INTERSPECIFIC TREE NAMED 'PLUMSWEET XI'

(50) Latin Name: ***Prunus* sp.**
Varietal Denomination: Plumsweet XI

(76) Inventor: Lowell Glen Bradford, 10237 E. Mariposa Way, Le Grand, CA (US) 95333

( * ) Notice: Subject to any disclaimer, the term of this patent is extended or adjusted under 35 U.S.C. 154(b) by 0 days.

(21) Appl. No.: 11/984,887

(22) Filed: Nov. 26, 2007

(51) Int. Cl.
*A01H 5/00* (2006.01)

(52) U.S. Cl. ..... Plt./180
(58) Field of Classification Search ..... Plt./180
See application file for complete search history.

(56) References Cited

U.S. PATENT DOCUMENTS

PP13,476 P2 1/2003 Bradford
PP15,809 P2 6/2005 Bradford

*Primary Examiner*—Annette H Para
*Assistant Examiner*—June Hwu

(57) ABSTRACT

The present invention relates to an interspecific tree and more particularly to a new and distinct variety broadly characterized by a medium to large size, vigorous, hardy, and productive tree. The present variety blooms in the early season, is self-unfruitful, requires cross pollination, but produces an abundance of pollen to entice bees. The fruit matures under the ecological conditions described during early July, with first picking on Jul. 1, 2007, and will hang on the tree for about fifteen more days. The fruit is uniformly medium to large in size, mostly red with orange yellow freckling in skin color, clingstone in type, oblate in shape, a red and yellow two-tone in flesh color, very firm and crisp in texture, and excellent in flavor.

1 Drawing Sheet

Botanical classification: *Prunus* sp.
Varietal denomination: 'Plumsweet XI'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits. The present invention relates to a new and distinct variety of interspecific tree, which has been denominated varietally as 'Plumsweet XI'.

During the 2003 growing season I gathered numerous plums having green skin from several different plum trees, most of which were in close proximity to apricots and interspecific fruit trees. The fruit from these plum trees was mixed, and the seeds were removed, cracked, stratified and germinated as a group with the label "Greenplum (OP)". They were grown as seedlings on their own root in my greenhouse and upon reaching dormancy transplanted to a cultivated area of my experimental orchard located near Le Grand, Calif. in Merced County (San Joaquin Valley). During the summer of 2006 the claimed variety was selected by me as a single plant from the group of seedlings described above. Subsequent to origination of the present variety of interspecific tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to 'Yummyrosa' (U.S. Plant Pat. No. 13,476) plum by being self-unfruitful and by producing fruit that is medium in size, that is clingstone in type, that is mostly dark red in skin color, and that is a red and yellow two-tone in flesh color, but is distinguished therefrom by blooming earlier and by producing fruit that is much firmer in texture, that is more oblate in shape, that is sweeter in flavor, and that matures about ten days later.

SUMMARY OF VARIETY

The present interspecific variety is characterized by a medium to large size, vigorous, hardy, and productive tree. Being self-unfruitful, the present variety requires cross pollination from an apricot, interspecific, or plum that blooms during the early season. The present variety's abundance of blossoms and pollen entices strong bee activity to facilitate pollination. The fruit matures under the ecological conditions described during early July, with first picking on Jul. 1, 2007, and will hang on the tree for about fifteen more days. The fruit is uniformly medium to large in size, mostly red with orange yellow freckling in skin color, clingstone in type, oblate in shape, a red and yellow two-tone in flesh color, very firm and crisp in texture, and excellent in flavor.

DRAWING

The accompanying photograph consists of four whole fruits positioned to display the characteristics of the skin color and form, two half fruits divided to reveal the flesh and stone, a young tip shoot growth, typical leaves, and two insets depicting the flower buds and blossoms as they appeared on the tree during the blooming season.

DETAILED BOTANICAL DESCRIPTION

Referring now more specifically to the pomological characteristics of this new and distinct variety of interspecific tree, the following has been observed under the ecological conditions prevailing near Le Grand, Merced County (San Joaquin Valley), Calif. The fruit description was developed at the state of full ripe on Jul. 14, 2007, on the original tree during its fourth growing season. The flower and bud descriptions were developed during the previous blooming season. All major color code designations are by reference to the Inter-Society Color Council, National Bureau of Standards. Common color names are also used occasionally.

Parentage

Seed parent: Unknown plum with green skin.
Pollen parent: Unknown.

Tree

Size: Medium to large, reaching and maintaining a height of 13' [3.96 m.] and a spread of 7' [2.13 m.] after four growing seasons utilizing typical dormant pruning.
Vigor: Vigorous, responding typically to irrigation and fertilization. The variety grows about 4' [1.22 m.] of surplus top-growth during the spring and summer. The plant should be grown on a standard commercial rootstock for production purposes.
Growth: Upright and dense.
Form: Pruned to a vase form.
Hardiness: Hardy with respect to central California winters.
Heat tolerance: Observed to perform adequately in typical central California climatic conditions, which typically include extended periods of heat.
Drought tolerance: Variety is developed for commercial orchards and requires regular irrigation.
Production: Very productive, thinning usually necessary.
Fertility: Self-unfruitful, requiring cross pollination by a suitable early to mid seasonal blooming apricot, interspecific, or plum, such as 'Yummy®gem' (U.S. Plant Pat. No. 15,809).
Bearing: Regular bearer, with no crop failures observed.
Trunk:
*Size.*—Medium, reaching a maximum diameter of 4" [102 mm.] after the fourth growing season.
*Texture.*—Shaggy.
*Bark color.*—A Dark yellowish brown [78. d.yBr] and Deep yellowish brown [75. deep yBr] variegation with Strong yellowish brown [74. s.yBr] crevices present.
*Lenticels.*—Approximate Number Per Square Inch: 5. Color: Strong yellowish brown [74. s.yBr]. Average Size: ¼" [6.4 mm.]. Shape: Eye-shaped, elongated.
Branches:
*Size.*—Diameter of limb is 2" [50.8 mm.] measured 12" above the crotch, 1" [25.4 mm.] measured 12" above the first fork.
*Texture.*—Smooth on first and second year wood, increasing roughness with age.
*Color.*—1st Year Wood Topside: Dark orange yellow [72. d.OY]. 1st Year Wood Underside: Brilliant yellow green [116. brill.YG]. Older Wood: Moderate brown [58. m.Br].
*Lenticels.*—Number Per Square Inch: More than 80 on second year wood. Color: Dark orange yellow [72. d.OY]. Average Size: 1/64" [0.4 mm.]. Shape: Elongated, rectangular.
Leaves:
*Size.*—Large. Average Length: 4⅛" [105 mm.]. Average Width: 2" [51 mm.].
*Arrangement.*—Alternate.
*Thickness.*—Medium.
*Form.*—Elliptical.
*Apex.*—Acuminate.
*Base.*—Acute with an average angle base angle of 75 degrees.
*Surface.*—Smooth.
*Color.*—Dorsal Surface: Moderate olive green [125. m.OlG]. Ventral Surface: Moderate yellow green [120. m.YG].
*Margin.*—Finely serrate.
*Venation.*—Pinnately net veined.
*Petiole.*—Average Length: ⅜" [9.5 mm.]. Average Thickness: 1/16" [1.6 mm.]. Color: Strong yellow green [117. s.YG] with Grayish reddish orange [39. gy.rO] areas where exposed to direct sunlight.
*Stipules.*—Number: 2 per leaf, up to 6 per growing tip. Average Length: ¼" [6.4 mm.]. Color: Very yellow green [115. v.YG] becoming Moderate reddish brown [43. m.rBr] with age.
*Glands.*—Number: Mostly 2 per leaf. Position: Alternately positioned at the intersection of the petiole and the leaf blade. Size: Medium to small. Form: Globose. Color: Brilliant yellow green [116. brill.YG] becoming Deep reddish brown [41. deep rBr] in the center with age. Leaf buds: Pointed, medium.
Flower buds:
*Hardiness.*—Hardy, with respect to central California winters.
*Diameter.*—Typically 3/16" [4.8 mm.] 1 week before bloom.
*Length.*—Typically ⅜" [9.5 mm.] 1 week before bloom.
*Form.*—Not appressed.
*Surface.*—Pubescent.
*Tip color.*—White [263. White].
Flowers: Perfect, complete, perigynous, usually a single pistil, typically thirty or more stamens, five sepals and petal locations alternately positioned.
*Average flower diameter.*—15/16" [23.8 mm.].
*Number of petals.*—Five, no double blossoms observed.
*Petal shape.*—Oval to circular.
*Petal margin.*—Entire, somewhat wavy with notches typical.
*Average petal diameter.*—7/16" [11.1 mm.].
*Average petal length.*—½" [12.7 mm.].
*Petal apex.*—Rounded.
*Petal base.*—Obtuse.
*Petal color.*—White [263. White] on both sides.
*Anther color.*—Very yellow [82. v.Y].
*Stigma color.*—Brilliant greenish yellow [98. brill.gY].
*Sepal color.*—Brilliant yellow green [116. brill.YG].
*Sepal length.*—⅛" [3.2 mm.].
*Sepal width.*—⅛" [3.2 mm.].
*Sepal apex.*—Rounded to elliptical to match the width and length.
*Sepal margin.*—Fairly smooth to the naked eye, slightly serrate when magnified.
*Average pistil length.*—11/16" [17.5 mm.], longer than normal.
*Average stamen length.*—½" [12.7 mm.].
*Fragrance.*—Moderate.
*Pollen production.*—Abundant, very bee enticing.
*Blooming period.*—Early, five days before 'Ambra' plum (unpatented).
*Onset of bloom.*—One percent on Feb. 17, 2007.

*Date of full bloom.*—Mar. 3, 2007.
*Duration of bloom.*—One to two weeks, dependent on ambient temperature.
*Bloom density.*—Heavy.
*Number per cluster.*—2 to 10, average 4.

FRUIT

Maturity when described: Firm ripe, Jul. 14, 2007.
Date of first picking: Jul. 1, 2007.
Date of last picking: Jul. 14, 2007.
Size: Uniform, medium to large.
*Average diameter axially.*—2⅛" [54.0 mm.].
*Average diameter across cheek plane.*—2 7/16" [61.9 mm.].
*Average diameter across suture plane.*—2 7/16" [61.9 mm.].
*Typical weight.*—5.1 ounces [145 grams].
Form: Uniform, oblate, some slightly asymmetrical.
*Longitudinal section form.*—Oblate.
*Transverse section through diameter.*—Round.
Suture: A distinct line located in a very shallow groove extending from the base to the apex.
Ventral surface: Rounded, slightly lipped on one side of the suture.
Lips: Unequal.
Cavity: Flaring, rounded, suture showing on one side, Dark grayish yellow [91. d.gy.Y] stem markings on some.
*Depth.*—5/16" [7.9 mm.].
*Breadth.*—⅞" [22.2 mm.].
Base: Truncate.
Apex: Truncate.
Pistil point: An inconspicuous dot.
Stem: Medium.
*Average length.*—⅜" [9.5 mm.].
*Average width.*—5/64" [2.0 mm.].
Skin:
*Thickness.*—Medium.
*Surface.*—Smooth.
*Tenacity.*—Tenacious to the flesh.
*Astringency.*—Slight.
*Tendency to crack.*—Slight.
*Color.*—Very dark red [17. v.d.R] with some Brilliant orange yellow [67. brill.OY] streaking on the shoulders with abundant Pale orange yellow [73. p.OY] freckling.
*Bloom.*—Abundant.
Flesh:
*Color.*—Dark red [16. d.R] toward the skin, Moderate yellow [87. m.Y] toward the stone.
*Surface of pit cavity.*—Covered with Light yellowish pink [28. l.yPk] broken fibers when twisted away from stone.
*Amygdalin.*—Moderate.
*Juice.*—Abundant, rich.
*Texture.*—Firm, crisp.
*Fibers.*—Abundant, fine and tender.
*Ripens.*—Slightly earlier toward the apex.
*Flavor.*—A tasty blend of acid and sugar, typically 22 brix.
*Aroma.*—Moderate.
*Eating quality.*—Excellent.

STONE

Type: Clingstone.
Form: Oval.
Hilum: Narrow.
Base: Straight.
Apex: Acute to acuminate with an average angle of 80 degrees and a sharp ⅛" [3.2 mm.] tip.
Sides: Equal.
Surface: Rough throughout with a groove from the base to the apex on each side of the dorsal fin.
External color of stone: Strong yellowish brown [74. s.yBr].
Pit wall color when cracked: Light yellowish brown [76. l.yBr].
Cavity surface color: Deep yellowish brown [75. deep yBr].
Average pit wall thickness: 1/16" [1.6 mm.].
Average width: 9/16" [14.3 mm.].
Average length: ⅞" [22.2 mm.].
Average breadth: ⅜" [9.5 mm.].
Tendency to split: None observed.
Kernel:
*Form.*—Oval.
*Skin color.*—Pale yellow [89. p.Y] when first removed.
*Pellicle color.*—Moderate yellowish brown [77. m.yBr].
*Vein color.*—Light yellowish brown [76. l.yBr].
*Taste.*—Bitter.
*Viable.*—Yes.
*Average width.*—⅜" [9.5 mm.].
*Average length.*—9/16" [14.3 mm.].
*Amygdalin.*—Moderate.

Use

Market: Fresh market and long distance shipping.
Keeping quality: Good, fruit quality observed to remain in good condition after 30 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of interspecific tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of interspecific *Prunus* sp. tree, substantially as illustrated and described, that is similar to 'Yummyrosa' (U.S. Plant Pat. No. 13,476) plum by being self-unfruitful and by producing fruit that is medium in size, that is clingstone in type, that is mostly dark red in skin color, and that is a red and yellow two-tone in flesh color, but is distinguished therefrom by blooming earlier and producing fruit that is much firmer in texture, that is more oblate in shape, that is sweeter in flavor, and that matures about ten days later.

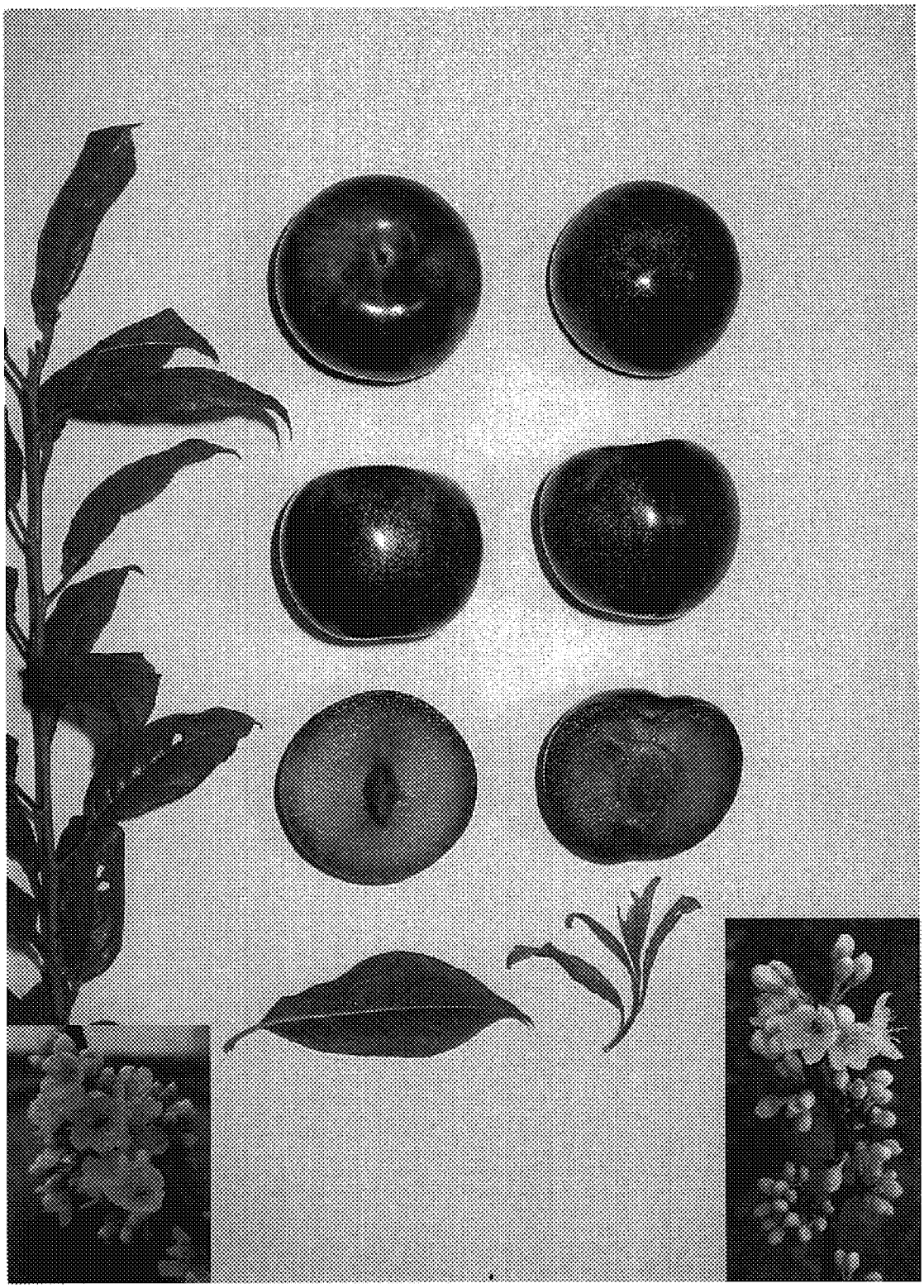

* * * * *